United States Patent [19]

Mikawa et al.

[11] Patent Number: 4,933,180

[45] Date of Patent: Jun. 12, 1990

[54] NOVEL ANTIBIOTIC VERMISPORIN, PROCESS FOR THE PRODUCTION THEREOF AND PHARMACEUTICAL COMPOSITION COMPRISING IT AS AN ACTIVE ANTIBACTERIAL AGENT

[75] Inventors: Takashi Mikawa, Sagamihara; Noriko Takahashi, Kawasaki; Haruyuki Ohkishi, Machida; Yoshikazu Sato, Tokyo; Shinji Miyadoh, Yokohama; Masaji Sezaki, Tokyo, all of Japan

[73] Assignees: Mitsubishi Kasei Corporation; Meiji Seika Kaisha, Limited, both of Tokyo, Japan

[21] Appl. No.: 151,611

[22] Filed: Feb. 2, 1988

[30] Foreign Application Priority Data

Feb. 3, 1987 [JP] Japan .................................. 62-22899

[51] Int. Cl.$^5$ ........................ A61K 35/70; G12P 1/02
[52] U.S. Cl. ................................................... 424/122
[58] Field of Search ......................... 424/122; 435/171

Primary Examiner—Jerome D. Goldberg
Attorney, Agent, or Firm—Oblon, Spivak, McClelland, Maier & Neustadt

[57] ABSTRACT

This disclosure describes a novel antibiotic designated Vermisporin produced in a microbiological fermentation using, for example, a new strain of Ophiobolus Vermisporus L-8. This novel antibiotic is an active antibacterial, especially anti-anaerobic bacterial agent.

10 Claims, 4 Drawing Sheets

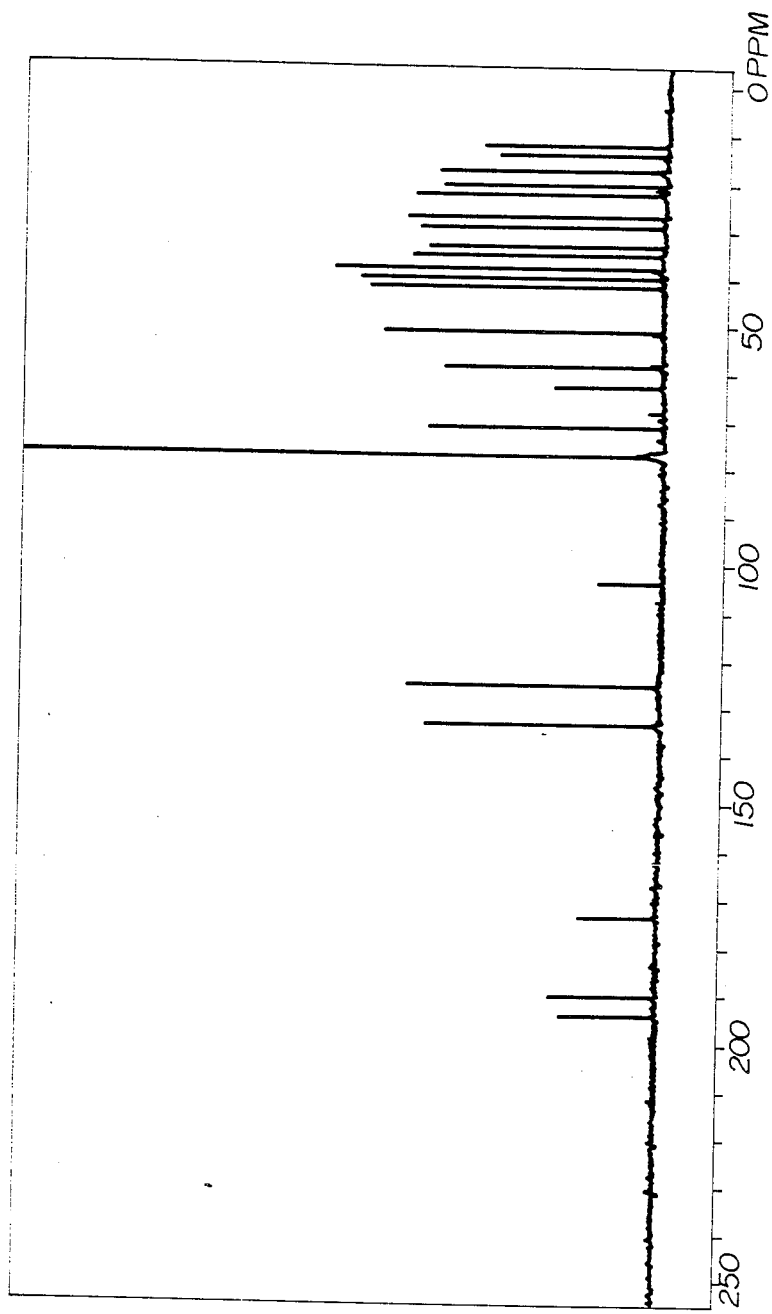

NOVEL ANTIBIOTIC VERMISPORIN, PROCESS FOR THE PRODUCTION THEREOF AND PHARMACEUTICAL COMPOSITION COMPRISING IT AS AN ACTIVE ANTIBACTERIAL AGENT

BACKGROUND OF THE INVENTION

1. Field of the Invention

The present invention relates to a novel antibiotic designated Vermisporin having antibacterial activities, especially against anaerobic bacteria, a process for the production thereof and a pharmaceutical composition comprising it as an active agent.

2. The Prior Art

Various kinds of antibiotics have been prepared and practically used in the fields of human and veterinary medicine, agriculture and the like. However, few materials showing effective antibacterial activities against anaerobic bacteria have been found, so that improved antibiotics are continually in demand in the field of therapeutics such as the treatment of human infectious diseases, swine dysentery and necrotic enteritis which are caused by anaerobic bacteria.

SUMMARY OF THE INVENTION

Through eraborate researches, the present inventors found that a substance having the desired antibacterial activities, especially strong antibacterial activities against anaerobic bacteria, was produced during the cultivation of a certain strain belonging to the genus Ophiobolus. The present inventors have further succeeded in isolating a novel antibiotic "Vermisporin" responsible for said activities and in determinating its physicochemical and biological properties.

Thus, one aspect of the present invention is to provide antibiotic Vermisporin.

In another aspect, the present invention provides a pharmaceutical composition useful in the treatment or prevention of infectious diseases caused by anaerobic bacteria comprising Vermisporin as an active agent.

Vermisporin according to the present invention has the following characteristics:

(a) an elemental composition:

| | |
|---|---|
| carbon | 70.18% |
| hydrogen | 8.73% |
| nitrogen | 3.10%; |

(b) a molecular weight:

415 (HR—MS m/Z 415.2719, M$^+$);

(c) a molecular formula:

$C_{25}H_{37}NO_4$;

(d) a specific rotation:

$[\alpha]_d^{20} = +73.8°$ (C 1.0, chloroform);

(e) an ultraviolet absorption spectrum determined in a methanol solution as shown in FIG. 1 with $\lambda_{max}^{MeOH}$ 229 nm ($\epsilon$ 6180), 291 nm($\epsilon$ 12280);

(f) an infrared absorption spectrum determined in a chloroform solution as shown in FIG. 2;

(g) proton NMR (400 MHz) spectrum determined in a deutero chloroform solution as shown in FIG. 3;

(h) a $^{13}$C NMR (100 MHz) spectrum determined in a deutero chloroform solution as shown in FIG. 4;

(i) solubility in chloroform, diethyl ether, acetone, ethyl acetate, methanol and ethanol, and insolubility in n-hexane and water;

(j) a color reaction:
positive against 10% sulfuric acid and molybdicacid reagents, and negative against Greig-Leaback reagent and ninhydrin reagent;

(k) an Rf value of 0.63 when subjected to thin-layer chromatography using a thin layer of silica gel (Art 5714) made by Merck Inc. and chloroform-methanol (30:1) as a developing solvent, and an Rf value of 0.52 when subjected to thin-layer chromatography using said thin layer and toluene-acetone (2:1) as a developing solvent;

(1) appearance:
colorless and oily.

In a further aspect, the present invention provides a process for the production of Vermisporin which comprises cultivating a Vermisporin-producing fungus of the genus Ophiobolus, and then recovering Vermisporin from the culture.

DESCRIPTION OF THE DRAWINGS

FIG. 4 shows a $^{13}$C NMR spectrum of Vermisporin in a deutero chloroform solution.

DETAILED DESCRIPTION

Figure 1:
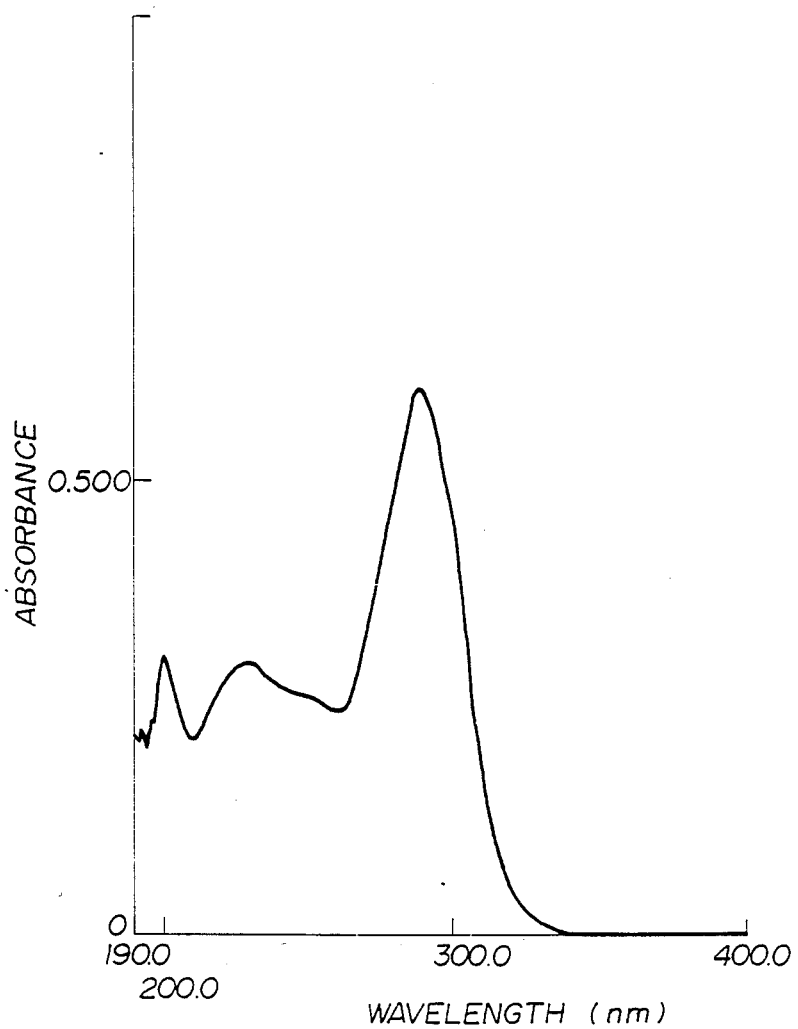
FIG. 1 shows an ultraviolet absorption spectrum of Vermisporin at a concentration of 20 μg/ml in a methanol solution.

The present invention will be described in detail below.

From the pattern of λmax in the ultraviolet absorption spectrum, it may be assumed that antibiotic Vermisporin of this invention has a tenuazonic-acid skeleton. From the comparison of the physicochemical and biological properties shown in Tables 1 & 2 of Vermisporin with those of the known antibiotics having tenuazonic acid-skeleton, it may be recognized that Vermisporin is a novel antibiotic.

The fungus, which may be used in the production of Vermisporin of this invention, is any which belongs to the genus Ophiobolus and is capable of producing Vermisporin sufficient enough to be recovered during the cultivation thereof. A typical example of such fungus is L-8 strain belonging to the class of Loculoascomycetes, which was first separated from a herbaceous plant body by the present inventors. The fungul properties of L-8 strain are as described below.

(1) Morphological characteristics:

Ascocarps grow sporadically or gregariously on a host plant. They initially grow buried beneath an epidermis of the host plant and then break through the epidermis so as to form necks projecting like a nipple. The ascocarps are spherical or semi-spherical and range 230–450 μm in diameter and 300–420 μm in height. The neck is 110–155 μm in diameter and 130–180 μm in length. On the inner face of a fovea at the neck there are colorless periphyses. A shell wall ranges 25–40 μm in thickness and composed of 5–10 layers of polygonal or rectangular cells. It forms a dark-brown and thick layer, and a light-colored and thin layer on the outer and inner shell wall, respectively. There generate many asci which are cylindrical or club-shaped, range 100–135×10–15 μm and taper off toward their proximal ends. An apical end thereof is round. The ascus is thick-walled and has double wall and 8 spores. Pseudoparaphyses are filiform and have a septum. Ascospores are arranged parallel to each other or twisted spirally in bundle in the ascus. The ascospore is club-like or long and cylindrical in shape, colorless and substantially straight or slightly curved, ranges 90–110 by 5–7 μm, and has usually seven septa. Each ascospore is neither significantly swollen nor constricted, and contains 1 to 3 oily droplet. Both poles of the ascospore have a gelatin-like appendage.

(2) Cultural characteristics on various media:

(a) Culture on potato-dextrose agar (PDA) medium at 27° C. for 10 days

Colonies expand to 2–3 cm in diameter in 10 days. Initially they shows a bright olive-grayish color, but later they become dark olive-gray. The basal hyphae extend radially and become branched. They reach 4.0–7.0 μm in width and have a septum. Many aerial hyphae are formed. No formation of the genital organ of perfect stage or imperfect stage is observed on the agar medium.

(b) Culture on malt agar (MA) medium at 27° C. for 10 days:

The cultural characteristics on this medium are the same as those on the PDA medium.

(3) Physiological properties:

(a) Optimum growth conditions pH: 6–7 (culturing in LCA liquid medium for 14 days);

Temperature: 27°–30° C. (culturing on PDA agar medium for 14 days);

(b) Possible growth conditions pH: 4–10 culturing in LCA liquid medium for 14 days);

Temperature: 20°–30° C. (culturing on PDA agar medium for 14 days);

(4) Classification of L-8:

(a) Taxonomical position in higher ranks

The present strain (L-8) grows in adhesion to a herbaceous plant and forms flask-shaped ascocarps. The asci are formed among the lasting pseudoparaphyses. The ascus have a double-wall structure. The ascospore is of multiple-septum structure. Based upon the above main characteristics, L-8 may be classified as the family Pleosporaceae of the order Pleosporales of the class Loculoascomycetes according to L. Holm, Symb. Botan. Upsal., 14(3), 1–188 (1957); Luttrell, Loculoascomycetes, The Fungi, Vol. 4A (ed. G. C. Ainsworth et al.), 135–219 (1973); J. A. von Arx and E. Müller, Stud. Mycol., 9, 1–159 (1975), etc.

(b) Identification in a genus rank

According to a literature in taxonomy, relating to the family Pleosporaceae by J. A. von Arx and E. Müller, ibidem, this family is subclassified into 77 genera. In these 77 genera, those having the long and cylindrical or filiform ascospores include Ophiobolus, Nodulosphaeria and Cochliobolus. These genera are distinguished from each other by such criteria as (1) the presence or absence of a seta on the outer face of ascocarp, (2) the presence or absence of a seta on the inner face of a fovea at the neck, (3) the presence or absence of a swollen ascospore, and (4) the presence or absence of conidium stage based on culture.

L-8 is characterized by (1) the absence of the seta on the outer face of the ascocarp, (2) the absence of the seta on the inner face of the fovea at the neck, (3) the absence of cylindrical swollen ascospores, and (4) non-formation of the conidium stage on various kinds of media.

In view of these characteristics, L-8 is identified as the strain of the genus Ophiobolus.

(c) Identication in a species rank

According to a taxonomical literature concerning the genus Ophiobolus by R. A. Shoemaker, Can. J. Bot., 54, 2365–2404 (1976), 31 species are enumerated as belonging to this genus. These species are distinguished from each other by features of their ascospores, i.e. shape and size of the spore, number of septa, the presence or absence of swollen cells, the presence or absence of a segmentation, the presence or absence of an appendage, color tone, etc.

L-8 has the following characteristics: (1) the ascospore is long and cylindrical or club-like in shape and 100–135×10–15 μm in size; (2) not swollen; (4) each ascospore won't segment lastingly; (5) the ascospore has, at its both poles, a gelatin-like appendage; and (6) the ascospore is colorless. These characteristics coincided with those of *Ophiobolus vermisporus* described in R. A. Shoemaker, Can. J. Bot., 54, 2393 (1976). Consequently L-8 was identified as *Ophiobolus vermisporus.*

The strain L-8 has been originally deposited under the accession number FERM P-9131 on Jan. 16, 1987 with the Fermentation Research Institute, the Agency of Industrial Science and Technology of the Ministry of International Trade and Industry.

The original deposit of L-8 was transferred to that under the Budapest Treaty on the International Recognition of the Deposit of Micro-Organisms for the Purpose of Patent Procedure on Dec. 24, 1987 under the accession number FERM BP-1636.

As is the case with other fungi, the characteristics of the fungi of the genus Ophiobolus are generally subject to variation. Therefore, not only the strain L-8 itself but also mutants and variants thereof (either spontaneous or induced), or even transformants or recombinants, may be used in this invention so long as they have the ability to produce antibiotic Vermisporin.

The culture medium employed to grow L-8 can be any one of a number of media containing nutrients assimilable by ordinary fungi. As a nutrient source, glucose, syrup, dextrin, sucrose, starch, molasses, animal and vegetable oils, and the like can be used. As the nitrogen source, soybean flour, wheat germ, corn-steep liquor, cottonseed cake, meat extract, peptone, yeast extract, ammonium sulfate, sodium nitrate, urea, and the like can be used. It may be also advantageous, if desired, to incorporate inorganic salts capable of yielding sodium, potassium, calcium, magnesium, cobalt, chloric, phosphoric, sulfuric and like ions. Further, there may be supplied suitable organic and inorganic substances that can promote the growth of the fungi and/or the production of antibiotic Vermisporin.

For the production of Vermisporin, an aerobic fermentation, especially a submerged aerobic fermentation is preferred. The Vermisporin-producing fungi may be suitably grown at 20°–30° C., although in many cases the cultivation is carried out at a temperature of about 26°–30° C. The amount of Vermisporin thus produced varies depending on the medium and culturing conditions. However, Vermisporin is usually accumulated to a maximum stage about in 3 to 10 days in both shaking culture and tank culture. When the accumulation of Vermisporin in the culture has reached the maximum, the incubation is terminated and then the culture is purified to isolate Vermisporin.

Since Vermisporin of this invention is a fat-soluble substance, the isolation and purification of Vermisporin from the culture may be accomplished by making use of that property. Thus, it is advantageous to employ solvent extraction using, for example, a synthetic sorbent such as Amberlite XAD-2 (Rohm & Haas) or Diaion HP-20 (Mitsubishi Chemical Industries Ltd.), a gel-filtering agent such as Sephadex LH-20 (Pharmacia) or Toyo-pearl HW-40 (Toyo Soda), ethyl acetate, chloroform or the like; column chromatography using silica-gel, alumina or the like; or preparative thin-layer chromatography using silica-gel as a carrier.

By using one of said methods alone or in combination with the others, it is possible to obtain highly purified Vermisporin having the physicochemical properties described above.

Detection of Vermisporin in each purification step may be carried out by a paper-disc assay using *Bacteroides fragilis* 2271 as an assay bacterium. In the paper-disc assay, the radius of growth inhibition circle on the agar medium is directly proportional to the logarithm of the concentration of Vermisporin at 20–700 $\mu$g/ml, giving 15–23 mm.

As shown in Tables 2 and 3 infra, Vermisporin of the present invention specifically inhibits the growth of anaerobic bacteria which are of a clinical problem in the field of obstetrics and gynecology and dental surgery. They are also notorious as pathogenic bacteria of serious infections including those in a digestive organ and opportunistic one. Thus, Vermisporin is useful in the treatment or prevention of these infections. In another aspect Vermisporin is useful in the treatment or prevention of animal diseases such as swine dysentery and necrotic enteritis.

When used in human, Vermisporin may be administered alone, or alternatively in combination with a pharmaceutically acceptable carrier. As a solid carrier, waxes such as polyethyleneglycol, whale wax and wood wax may be employed. As a liquid carrier, there may be mentioned alcohols such as ethanol, glycol and glycerol, and glycolethers such as ethyleneglycol monomethylether, diethyleneglycol and monomethylether. Vermisporin may be further combined with known additives such as a diluent, a thickener or a stabilizer. Among the dosage forms, there may be mentioned, for example, powder, tablet, capsule, emulsion and ointment. Such dosage forms usually comprise from 50 mg to 500 mg of Vermisporin. Vermisporin is administered to human orally or parenterally at rates of from 2–300 mg/subject/day to about 2–3 g/subject/day, preferably from about 200 mg/subject/day to about 1000 mg/subject/day.

On the other hand, when used in animals, Vermisporin may be directly mixed with feed for animal, or the pharmaceutical composition comprising Vermisporin mixed with a pharmaceutically acceptable carrier such as defatted bran, soybean flour, rice bran, ground corn, oil cake and lactose may be administered to the animals. The concentration of Vermisporin is generally in the range of about 1 to about 100 ppm in the feed or about 1 to about 50% in the pharmaceutical composition. The carriers and dosage forms used in the pharmaceutical composition are similar to those used in human.

The novel antibiotic Vermisporin of this invention has excellent antibacterial activities, especially against gram-positive bacteria and anaerobic bacteria, and may be used as an antibacterial agent.

The following Examples illustrate the invention but are not to be construed as limiting the scope thereof.

EXAMPLE 1

40 ml of medium (pH 6.0) containing 2.0% of syrup, 0.3% of soybean oil, 1.2% of soybean flour, 1.2% of wheat germ, 0.02% of $Na_2SO_4$, 0.0005% of $FeSO_4.7H_2O$, 0.005% of $CoCl_2.6H_2O$ and 0.1% of $CaCO_3$ was pipetted into each of the twenty 200 ml three-necked flasks, which were then subjected to sterilization in an autoclave at 121° C. for 20 minutes.

The medium in each flask was inoculated with one platinum loopful of *Ophiobolus vermisporus* L-8 strain which is the Vermisporin-producing strain. The inoculated medium was incubated at 26° C. for 4 days on a shaker rotating at 210 r.p.m., and then served as a seed culture.

80 ml of the same medium as the above was pipetted into each of the 100 three-necked flasks of 500 ml and subjected to sterilization in the autoclave at 121° C. for 20 minutes. These main fermentation media were inoculated respectively with 4 ml of said seed culture and incubated at 26° C. for 5 days on a shaker rotating at 210 r.p.m. The resulting culture was centrifuged to give a supernatant of the culture and a fungul cake.

EXAMPLE 2

The fungul cake was extracted with 1.5 liter of a 70% acetone aqueous solution at room temperature for one hour. The extract was filtered to remove the fungi and the filtered extract was concentrated upto 0.3 liter, which was then combined with 4.7 liter of the supernatant obtained in Example 1. A 5 liter portion of solution thus prepared was further extracted with an equal volume of ethyl acetate. The extract was washed with water, dehydrated over anhydrous sodium sulfate and concentrated under reduced pressure to obtain 7.12 g of an oily substance. This oily substance was combined with 7.5 g of diatomaceous earth, dried overnight under reduced pressure and charged on a column of 300 ml of silica gel C-200 (Wako Pure Chemical Industries Ltd.) prepared in chloroform. The column was washed with chloroform, and eluted with a chloroform-methanol (100:1) mixture and then with a chloroform-methanol (50:1) mixture. The active fractions were collected, concentrated under reduced pressure and evaporated to dryness to obtain 1.29 g of an oily substance. This oily substance was again subjected to chromatography using the silica gel C-200, in which after washing with chloroform, the column was eluted with a chloroform-methanol (100:1) mixture to obtain again the active fractions. The collected active fractions were concentrated under reduced pressure and evaporated to dryness to obtain 709 mg of an oily substance. This oily substance was dissolved in a small amount of methanol, charged on a methanol-filled column of 1 liter of Sephadex LH-20 (Pharmacia) and eluted with methanol. The active substance was eluted out in fraction Nos. 38–44 by 12-ml fractionation. These active fractions were collected, concentrated under reduced pressure and evaporated to dryness to obtain 481 mg of an oily substance. 220 mg of this oily substance was subjected to preparative thin-layer chromatography (developing solvent: chloroform/methanol=30/1) using a silica gel plate (Merck Inc.). The active fractions were extracted with methanol and then methanol was removed under reduced pressure to obtain 66 mg of an oil substance. This oily substance was dissolved in a small quantity of methanol. The resulting methanol solution was charged on a methanol-filled column of 300 ml of Sephadex LH-20 and eluted with methanol. The active substance was eluted out in fraction Nos. 31–36 by 5.5 ml-fractionation. These active fractions were collected, concentrated under reduced pressure and evaporated to dryness to obtain 31 mg of crude Vermisporin as an oily substance. This crude Vermisporin was dissolved in 10 ml of chloroform, washed with an equal amount of acidic water of pH 2, further washed with water, then dehydrated over anhydrous sodium sulfate, concentrated under reduced pressure and evaporated to dryness to obtain 28 mg of purified Vermisporin as a colorless oily substance. The physicochemical properties of this substance are as described before.

In each purification step, the active fractions were determined by the afore-mentioned paper-disc assay using *Bacteroides fragilis* 2271 as the assay bacterium.

The acute toxicity ($LD_{50}$) of the purified Vermisporin, as determined by intraperitoneally administering it to mice by a conventional method, was over 100 mg/kg.

EXAMPLE 3

The test bacteria of $10^6$ CFU/ml each shown in Table 1 were subjected to aerobic culture at 37° C. for 18 hours according to the standard method of Japan Society of Chemotherapy by using GAM agar medium (Nissui Pharmaceutical Co., Ltd.). The radii of growth inhibition circles were then measured to determine the minimal inhibitory concentrations of Vermisporin of this invention against said test bacteria. The results are shown in Table 1.

TABLE 1

| Test bacteria | Minimal inhibitory concentration (μg/ml) |
| --- | --- |
| Staphylococcus aureus 209p JC-1 | 3.13 |
| Staphylococcus aureus Smith S-424 | 3.13 |
| Staphylococcus aureus No. 26 | 3.13 |
| Staphylococcus epidermidis ATCC 14990 | 3.13 |
| Staphylococcus epidermidis 109 | 3.13 |
| Enterococcus faecalis ATCC 8043 | 3.13 |
| Bacillus anthracis No. 119 | 0.78 |
| Escherichia coli NIHJ JC-2 | >100 |
| Salmonella typhi 0-901-W | >100 |
| Klebsiella pneumoniae PCI 602 | >100 |
| Pseudomonas aeruginosa MB 3829 | >100 |
| Pseudomonas cepacia M-0527 | >100 |

EXAMPLE 4

The test bacteria of $10^6$ CFU/ml each shown in Table 2 were subjected to anaerobic culture at 37° C. for 48 hours by using the GAM agar medium. The radii of growth inhibition circles were then measured to determine the minimal inhibitory concentrations of Vermisporin of this invention against said test bacteria. The results are shown in Table 2.

TABLE 2

| Test bacteria | Minimal inhibitory concentration (μg/ml) |
| --- | --- |
| Bacteroides fragilis NCTC 9343 | 0.78 |
| Bacteroides fragilis GM-7000 | 0.78 |
| Bacteroides fragilis C-2 | 0.78 |
| Bacteroides melaninogenicus ATCC 25260 | 0.78 |
| Bacteroides melaninogenicus NCTC 9337 | 0.39 |
| Bacterodies melaninogenicus NCTC 9338W | 0.39 |
| Bacteroides praeactus ATCC 25539 | 0.39 |
| Bacteroides ruminicola C-12 | 0.20 |
| Bacteroides distasonis E-32 | 0.78 |
| Bacteroides ovatus ATCC 8483 | 0.78 |
| Bacteroides frucosus ATCC 25662 | 1.56 |
| Eubacterium lentum ATCC 25559 | 1.56 |
| Eubacterum limosum ATCC 8486 | 3.13 |
| Eubacterium aerofaciens ATCC 25986 | 6.25 |
| Propionibacterium acnes ATCC 6919 | 0.39 |
| Clostridium difficile No. 51 | 0.78 |
| Clostridium difficile No. 53 | 0.78 |
| Clostridium difficile No. 55 | 0.78 |
| Clostridium difficile No. 57 | 0.78 |
| Clostridium difficile No. 59 | 1.56 |
| Clostridium difficile No. 72 | 1.56 |
| Clostridium difficile No. 74 | 0.78 |
| Clostridium difficile No. 76 | 0.78 |
| Clostridium difficile No. 78 | 0.78 |
| Clostridium difficile No. 80 | 0.78 |
| Clostridium difficile No. 82 | 1.56 |
| Clostridium difficile No. 84 | 0.78 |
| Clostridium difficile No. 88 | 1.56 |
| Clostridium difficile No. 90 | 0.78 |
| Clostridium difficile No. 92 | 0.78 |
| Clostridium tetani G-41 | 0.78 |
| Clostridium perfringens JAM 3-2 | 1.56 |
| Clostridium sporogenes No. 1 | ·1.56 |
| Actinomyces naeslundii ATCC 12104 | 0.20 |
| Bifidobacterium adolescentis ATCC 15705 | 6.25 |
| Peptostreptococcus saccharolyticus ATCC 14953 | 0.78 |
| Peptostreptococcus parvulus Moore 5229 | 6.25 |
| Peptostreptococcus micros Moore 5462 | 0.05 |
| Peptostreptococcus assaccharolyticus R-16 | 0.10 |

EXAMPLE 5

Swine dysentery bacteria shown in Table 3 on the TS agar medium (Difco Co.) supplemented with 5% horse blood were incubated in an anaerobic condition at 37° C. for 5 days. The TS media containing 5% of horse blood and a series of dilutions of Vermisporin in Petri dishes were inoculated with 5 μl of the above bacteria of $10^6$ CFU/ml, which had been scraped from the TS medium. These inocula were incubated in an anaerobic condition at 37° C. for 5 days Colony formation and hemolysis in each dish were detected so as to determine the minimal inhibitory concentrations of Vermisporin. The results are shown in Table 3.

TABLE 3

| Test bacteria | Minimal inhibitory concentration (μg/ml) |
| --- | --- |
| Treponema hyodysenteriae PF-9 $P_1$ | 0.78 |
| Treponema hyodysenteriae PF-9 $P_2$ | 0.78 |
| Treponema hyodysenteriae PF-9 $P_3$ | 0.78 |
| Treponema hyodysenteriae YD-3 $P_1$ | 0.10 |
| Treponema hyodysenteriae YD-3 $P_2$ | ≦0.05 |

Figure 2:
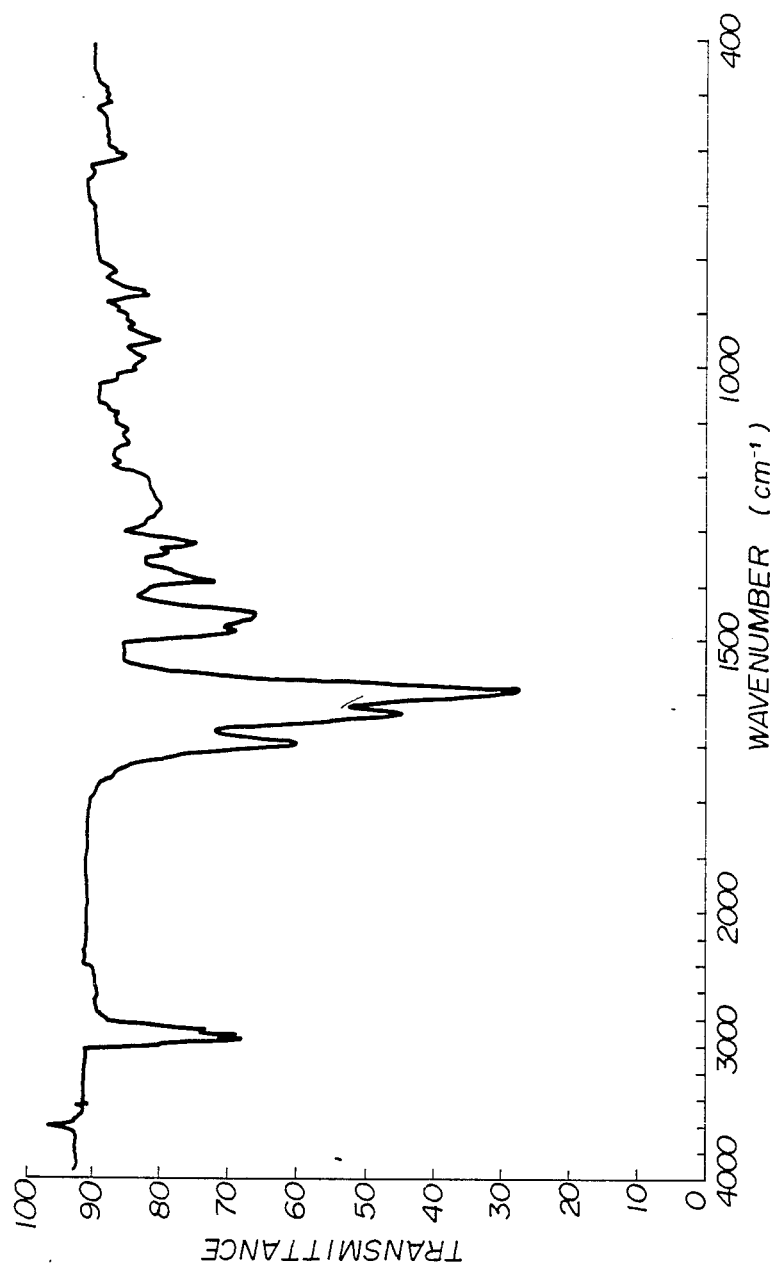
FIG. 2 shows an infrared absorption spectrum of Vermisporin in a chloroform solution.
Figure 3:
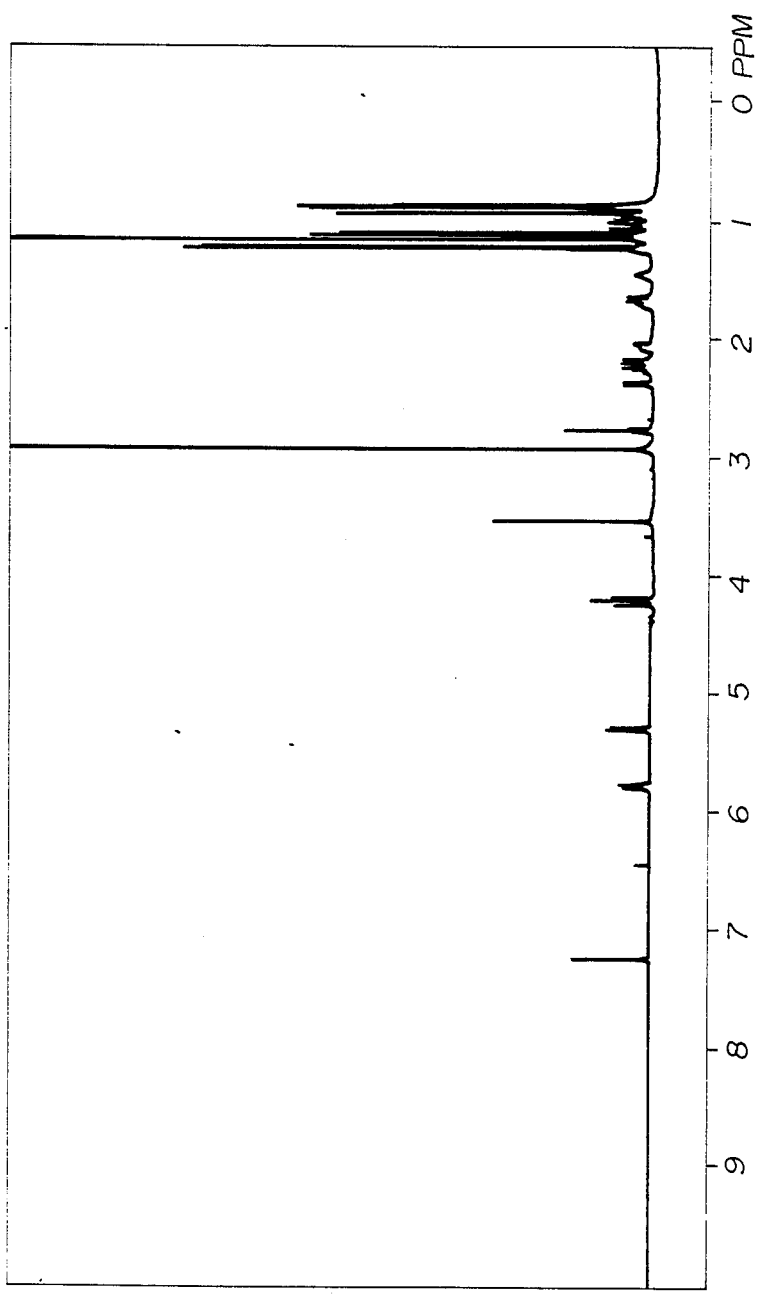
FIG. 3 shows a proton NMR spectrum of Vermisporin in a deutero chloroform solution.

What is claimed is:
1. Antibiotic Vermisporin having the following characteristics:

(a) an elemental composition:
   carbon 70.18%
   hydrogen 8.73%
   nitrogen 3.10%;
(b) a molecular weight:

415 (HR—MS, m/Z 415.2719, M$^+$);

(c) a molecular formula:

$C_{25}H_{37}NO_4$;

(d) a specific rotation:

$[\alpha]_D^{20} = +73.8°$ (C 1.0, chloroform);

(e) an ultraviolet absorption spectrum determined in a methanol solution as shown in FIG. 1 with $\lambda_{max}^{MeOH}$ 229 nm ($\epsilon$ 6180),
   291 nm ($\epsilon$ 12280);

(f) an infrared absorption spectrum determined in a chloroform solution as shown in FIG. 2;
(g) a proton NMR (400 MHz) spectrum determined in a deutero chloroform solution as shown in FIG. 3;
(h) a $^{13}$C NMR (100 MHz) spectrum determined in a deutero chloroform solution as shown in FIG. 4;
(i) solubility in chloroform, diethyl ether, acetone, ethyl acetate, methanol and ethanol; and insolubility in n-hexane and water;
(j) a color reaction: positive against 10% sulfuric acid and molybdic acid reagents, and negative against Greig-Leaback reagent and ninhydrin reagent;
(k) an Rf value of 0.63 when subjected to thin-layer chromatography using a thin layer of silica gel (Art 5714) made by Merck Inc. and chloroform-methanol (30:1) of 0.52 when subjected to thin-layer chromatography using said thin layer and toluene-acetone (2:1) as a developing solvent;
(l) appearance: colorless and oily.

2. A pharmaceutical composition for use in the treatment or prevention of infectious diseases caused by anaerobic bacteria, comprising; an antibacterially effective amount of Vermisporin as defined in claim 1 and a pharmaceutically acceptable carrier therefor.

3. The composition of claim 2, wherein said vermisporin is present in the composition in an amount ranging from 1 to 50%.

4. A method of treating an animal or human suffering from an infection caused by an anaerobic bacterium, comprising:
   administering to said subject an antibacterially effective amount of Vermisporin as defined in claim 1.

5. The method of claim 4, wherein said human is administered from 2–300 mg/day to about 2–3 g/day of said vermisporin.

6. A method of producing vermisporin as defined in claim 1, comprising:
   cultivating the Vermisporin-producing fungus strain *Ophiobolus vermisporus* BP-1636 in a growth promoting medium under aerobic conditions at a temperature ranging from 20°–30° C. for 3 to 10 days; and
   recovering Vermisporin from the growth medium.

7. The method of claim 6, wherein said growth medium is potato-dextrose agar or malt agar.

8. The method of claim 6, wherein the growth medium contains glucose, syrup, dextrin, sucrose, starch, molasses or animal and vegetable oils as the nutrient source.

9. The method of claim 6, wherein the growth medium contains soybean flour, wheat germ, corn-steep liquor, cottonseed cake, meat extract, peptone, yeast extract, ammonium sulfate, sodium nitrate or urea as the nitrogen source.

10. The method of claim 6, wherein the growth medium contains sodium, potassium, calcium, magnesium, cobalt, chloride, phosphate, sulfate or combinations thereof as inorganic ions.

* * * * *